July 19, 1960 C. D. CORLISS Plant Pat. 1,960
EUONYMUS PLANT
Filed Oct. 6, 1959
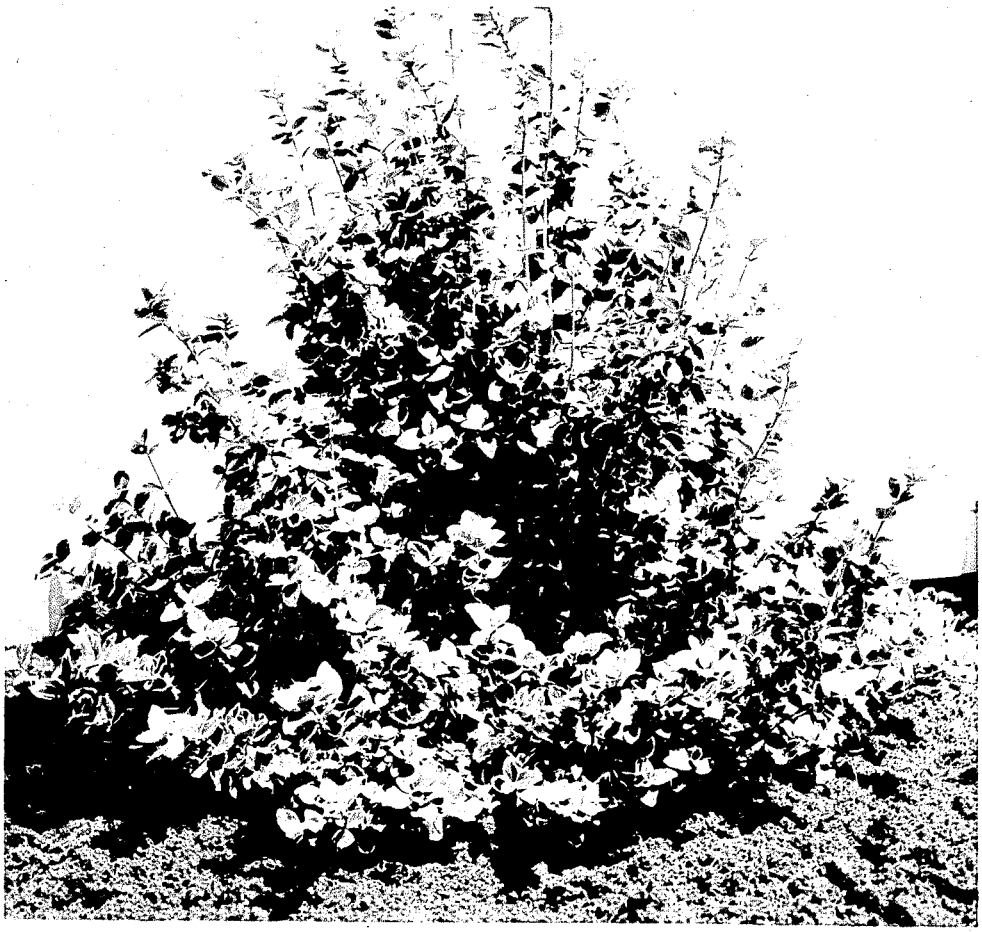
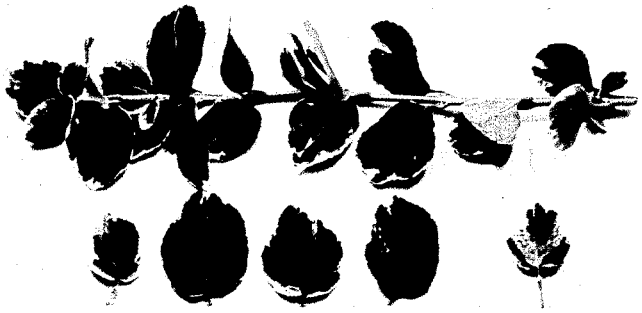
INVENTOR
Clifford D. Corliss
By Orville M. Kile
Plant Patent Agt.

United States Patent Office

Plant Pat. 1,960
Patented July 19, 1960

1,960

EUONYMUS PLANT

Clifford D. Corliss, Gloucester, Mass., assignor to Corliss Bros. Incorporated, Gloucester, Mass., a corporation of Massachusetts Filed Oct. 6, 1959, Ser. No. 844,839

1 Claim. (Cl. 47—59)

My present discovery relates to a new and distinct variety of *Euonymus fortunei* plant which occurred as a sport of one of the younger plants of Emerald Pride (Plant Patent 1,073), growing in our nurseries at Ipswich, Massachusetts. Plants produced asexually at Ipswich by means of cuttings appear to have the same characterics as the original sport.

While this new variety possesses many of the qualities of its parent, it is outstandingly different because of the pronounced white margin on its dark green leaves. It is a well-shaped, compact, evergreen shrub and possesses great decorative value throughout the year. The variety is apparently resistant to disease and drought conditions, since none of the present four year old plants have been affected. Also, it has been able to withstand extreme winter conditions of frozen, icy ground. These four year old plants, unprotected, lived over the winter 1958–59 when temperatures went down to zero and below and the ground was frozen solid from November to April, while other broadleaf evergreens, such as mountain laurel, rhododendron, and hollies, succumbed to these extreme conditions. The parent plant has lived through temperatures of more than 20 degrees below zero.

The accompanying illustrations show in color photographs a typical four year old plant of this new variety, clearly displaying the white-margined leaves, which are also shown in greater detail at the bottom of the illustration.

In the following detailed description, color references indicate Nickerson's Color Fan. Where no reference is given, the usual dictionary meaning is intended.

Form: Erect, compact, shapely, upright shrub, growing from central stem without support.

Growth: Present size of plant is 2½ feet high by 2 feet in spread, but is expected to grow to a height of 4 to 5 feet since its parent did not reach a height of 4 feet until 14 years old and in the following 9 years added another foot in height.

Hardiness: Particularly resistant to extreme cold, as set forth above.

Stems or branchlets:

*Surface.*—Minutely warty, with few aerial rootlets.

*Color.*—Near moderate yellow green (5 GY 5/6).

*Axillary buds.*—Conical, with bud scales looser than on parent variety.

Foliage:

*Type.*—Broadleaf evergreen; opposite; petioled.

*Shape.*—Round to ovate, base rounded; apex obtuse to emarginate.

*Petioles.*—5 to 7 mm. long; color same as stem.

*Size of leaf.*—3 to 4 cm. long; 2 to 3 cm. wide.

*Texture.*—Heavy; smooth.

*Veining.*—Veins generally lighter in color and with raised midrib.

*Serrations.*—Margins crenate-serrate.

*Color.*—Upper surface grayish olive green (7.5 GY 3/2) with pronounced white to cream margins, irregular in depth, usually ranging from 1 to 5 mm. in depth. Under surface near moderate yellow green (2.5 GY 5/5). Leaf tends toward slight pinkish cast in late fall, thus adding richness and depth to the appearance of the shrub.

Flowers: Inconspicuous; white; borne in axillary cymes.

*Berry or fruit*

Capsules:

*Quantity.*—8 to 10 in a cluster.

*Size.*—Large.

*Surface.*—Slightly warty.

*Shape.*—Lobed; sub-globose; average 3-celled.

*Color.*—Pale orange yellow (75 YR 9/4), splitting open at maturity to expose hanging seeds covered with aril.

Aril:

*Color.*—Bright reddish-orange (10 R 6/12).

*Appearance.*—Shiny.

*Position.*—Covering white seeds which are contained within the capsule.

Having thus disclosed my discovery, I claim:

The new and distinct variety of *Euonymus fortunei* plant, substantially as herein shown and described, characterized particularly by its shapely, erect, shrub growth from a central stem; its thick foliage of rich, dark green leaves having pronounced white to cream colored margins of irregular depth, and having in late fall a slight pinkish cast; its ability to withstand unusually low winter temperatures; and its apparent resistance to disease and drought condition.

No references cited.